United States Patent
Wu et al.

(10) Patent No.: US 10,626,116 B2
(45) Date of Patent: Apr. 21, 2020

(54) CRYSTALLINE FORM OF BTK KINASE INHIBITOR AND PREPARATION METHOD THEREOF

(71) Applicant: Jiangsu Hengrui Medicine Co., Ltd., Lianyungang, Jiangsu (CN)

(72) Inventors: Guaili Wu, Jiangsu (CN); Zhenjun Qiu, Jiangsu (CN); Xi Lu, Jiangsu (CN); Yun Lu, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 16/067,229

(22) PCT Filed: Dec. 20, 2016

(86) PCT No.: PCT/CN2016/111051
§ 371 (c)(1),
(2) Date: Jun. 29, 2018

(87) PCT Pub. No.: WO2017/118277
PCT Pub. Date: Jul. 13, 2017

(65) Prior Publication Data
US 2019/0010161 A1    Jan. 10, 2019

(30) Foreign Application Priority Data

Jan. 5, 2016   (CN) .......................... 2016 1 0006080

(51) Int. Cl.
| C07D 487/04 | (2006.01) |
| A61P 35/00 | (2006.01) |
| A61P 37/00 | (2006.01) |
| A61P 37/02 | (2006.01) |

(52) U.S. Cl.
CPC ............ *C07D 487/04* (2013.01); *A61P 35/00* (2018.01); *A61P 37/00* (2018.01); *A61P 37/02* (2018.01); *C07B 2200/13* (2013.01)

(58) Field of Classification Search
CPC .................................................. C07D 487/04
See application file for complete search history.

(56) References Cited

U.S. PATENT DOCUMENTS

| 8,673,925 B1 | 3/2014 | Goldstein |
| 10,323,037 B2 * | 6/2019 | Liu ...................... C07D 487/04 |

FOREIGN PATENT DOCUMENTS

| CN | 101674834 A | 3/2010 | |
| CN | 102711765 A | 10/2012 | |
| WO | 2007138355 A1 | 12/2007 | |
| WO | 2014036016 A1 | 3/2014 | |
| WO | 2016007185 A1 | 1/2016 | |
| WO | WO-2016007185 A1 * | 1/2016 | .......... C07D 487/04 |
| WO | WO-2018210296 A1 * | 11/2018 | ......... A61K 31/4545 |

OTHER PUBLICATIONS

H.G. Brittain, in Polymorphism in Pharmaceutical Solids (H.G. Brittain ed., 2nd ed., 2009) (Year: 2009).*
A.Y. Lee et al., 2 Annual Review of Chemical and Biomolecular Engineering, 259-280 (2011) (Year: 2011).*
G.P. Stahly, 7 Crystal Growth & Design, 1007-1026 (2007) (Year: 2007).*
Bohumil Kratochvi´l, Solid Forms of Pharmaceutical Molecules in, Glassy, Amorphous and Nano-Crystalline Materials (J. Simon ed., 2011) (Year: 2011).*
G. Van den Mooter, 9 Drug Discovery Today: Technologies, e79-e85 (2012) (Year: 2012).*
S.L. Morissette et al., 56 Advanced Drug Delivery Reviews, 275-300, 276 (2004) (Year: 2004).*
A.M. Campeta et al., 99 Journal of Pharmaceutical Sciences, (2010) (Year: 2010).*
S. Singhal et al., 56 Advanced Drug Delivery Reviews, 335-347 (2004) (Year: 2004).*
R. Tripathi et al., 11 AAPS PharmSciTech, (2010) (Year: 2010).*
M. Boukerche et al., 88 Chemical Engineering Research and Design, 1474-1478 (2010) (Year: 2010).*
A. Cote et al., 13 Organic Process Research & Development, 1276-1293 (2009) (Year: 2009).*
S. Datta et al., 3 Nature Reviews | Drug Discovery, 42-57 (2004) (Year: 2004).*
Int'l Search Report dated Mar. 23, 2017 in Int'l Application No. PCT/CN2016/111051.

* cited by examiner

*Primary Examiner* — Alexander R Pagano
(74) *Attorney, Agent, or Firm* — Ice Miller LLP

(57) ABSTRACT

The present invention relates to a crystalline form of a BTK kinase inhibitor and the preparation method thereof. In particular, the present invention relates to a crystal form I of (R)-4-amino-1-(1-(but-2-ynoyl)pyrrolidin-3-yl)-3-(4-(2,6-difluorophenoxy)phenyl)-1 H-pyrrolo[2,3-d]pyridazin-7 (6H)-one (the compound of formula (I)) and the preparation method thereof. The crystal form I of the compound of formula (I) obtained by the present invention has a good crystalline stability and chemical stability, and the crystallization solvent used has a low toxicity and low residue, thus making it more suitable for use in clinical treatment.

11 Claims, 4 Drawing Sheets

CRYSTALLINE FORM OF BTK KINASE INHIBITOR AND PREPARATION METHOD THEREOF

CROSS-REFERENCE TO RELATED APPLICATION

This application is a Section 371 of International Application No. PCT/CN2016/111051, filed Dec. 10, 2016, which was published in the Chinese language on Jul. 13, 2017, under International Publication No. WO 2017/118277 A1, which claims priority under 35 U.S.C. § 119(b) to Chinese Application No. 201610006080.0, filed Jan. 5, 2016, the disclosures of which are incorporated herein by reference in their entirety.

FIELD OF THE INVENTION

The present invention relates to a crystalline form of a BTK kinase inhibitor and a preparation method thereof. Specifically, the present invention relates to a crystal form of (R)-4-amino-1-(1-(but-2-ynoyl)pyrrolidin-3-yl)-3-(4-(2,6-difluorophenoxy)phenyl)-1 H-pyrrolo[2,3-d]pyridazin-7 (6H)-one and a preparation method thereof. The compound of formula (I) prepared according to the method of present invention can be used in the treatment of B-cell malignancies and autoimmune diseases.

BACKGROUND OF THE INVENTION

Immune cells can usually be divided into T cells and B cells, wherein the main function of B cells is to secrete various antibodies to protect the body against all kinds of foreign invasion. Bruton tyrosine protein kinase (BTK) is a member of the tyrosine protein kinase subfamily, and belongs to the Tec family kinase. It is mainly expressed in B cells, and distributed in the lymphatic system, hematopoietic and hematological systems. B-cell receptor (BCR) plays a crucial role in regulating the proliferation and survival of various lymphomas selected from subtypes of chronic lymphocytic leukemia (CLL) and non-Hodgkin lymphoma (NHL), mantle cell lymphoma (MCL), and diffuse large B-cell lymphoma (DLBCL). In addition, the effects of B cells in the pathogenesis of rheumatoid arthritis, systemic lupus erythematosus, multiple sclerosis, and other immune diseases have been proven in clinical practice. Bruton tyrosine protein kinase (BTK) is a key protein kinase in the BCR signaling pathway. It is capable of regulating the maturation and differentiation of normal B cells, and is also closely related to various diseases of B cell lymphoid tissue disorders. Therefore, the small molecule inhibitor targeting BTK can be beneficial to the treatment of B-cell malignancies and autoimmune diseases.

Ibrutinib is the first-generation of small molecule inhibitor of BTK developed jointly by Pharmacyclics and Janssen. It was first approved by the FDA for the treatment of mantle cell lymphoma (MCL) in November 2013, and was subsequently approved for the treatment of chronic lymphocytic leukemia (CLL) in February 2014. Ibrutinib binds irreversibly to the cysteine 481 of ATP-binding domain on the BTK kinase through its Michael receptor, thereby inhibiting the downstream signal transmission of BTK, and effectively controlling the growth of tumor cells.

PCT/US14/61393 relates to a compound of formula (I), i.e., (R)-4-amino-1-(1-(but-2-ynoyl)pyrrolidin-3-yl)-3-(4-(2,6-difluorophenoxy)phenyl)-1H-pyrrolo[2,3-d]pyridazin-7(6H)-one. This compound is a novel BTK kinase inhibitor, and has improved kinase selectivity, clinical efficacy or indications, and safety. However, no study was performed on the crystalline form of the compound in this patent application.

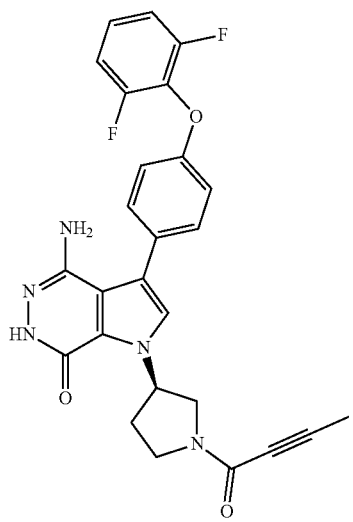

Formula (I)

The crystal structure of a pharmaceutically active ingredient often affects the chemical stability of the drug. Different crystallization conditions and storage conditions may lead to changes in the crystal structure of the compound, and sometimes accompanying production of other crystal forms. In general, an amorphous drug product does not have a regular crystal structure, and often has other defects, such as poor product stability, finer crystallization, difficult filtration, easy agglomeration, and poor liquidity. Therefore, it is necessary to improve the various properties of the above product. There is a need to find a new crystal form with high purity and good chemical stability.

SUMMARY OF THE INVENTION

The object of the present invention is to provide crystal form I of (R)-4-amino-1-(1-(but-2-ynoyl)pyrrolidin-3-yl)-3-(4-(2,6-difluorophenoxy)phenyl)-1H-pyrrolo[2,3-d] pyridazin-7(6H)-one and a preparation method thereof. The applicant has investigated a series of crystal products of the compound of formula (I) obtained under various crystallization conditions, and X-ray diffraction and differential scanning calorimetry (DSC) measurements have been conducted on the obtained crystal products. It was found that a stable crystal form, which is referred to as crystal form I, can be obtained under the crystallization condition of the present invention. The DSC spectrum of crystal form I of the present application shows a melting endothermic peak at about 236.23° C. The X-ray powder diffraction spectrum represented by 2θ angle and interplanar distance is obtained by using Cu-Kα radiation, in which there are characteristic peaks at 2θ±0.2: 9.91, 12.20, 17.24, 17.64, and 21.48.

Further, the crystal form I has characteristic peaks at 2θ±0.2: 7.86, 9.91, 12.20, 13.73, 17.24, 17.64, 19.02, 19.93, 20.72, 21.48, 22.64, 24.81, 27.44, and 27.87.

Further, the X-ray powder diffraction spectrum of the crystal form I is shown in FIG. 3, in which there are characteristic peaks at 2θ±0.2: 5.11 (17.30), 7.86 (11.24), 9.91 (8.92), 12.20 (7.25), 13.73 (6.45), 15.44 (5.73), 17.24

(5.14), 17.64 (5.02), 19.02 (4.66), 19.93 (4.45), 20.72 (4.28), 21.48 (4.13), 22.64 (3.92), 23.12 (3.84), 24.81 (3.59), 25.43 (3.50), 26.24 (3.39), 27.44 (3.25), 27.87 (3.20), and 29.03 (3.07).

The present invention also provides a method for preparing the crystal form I of the compound of formula (I). Specifically, the method comprises the following steps:

1) dissolving a solid (R)-4-amino-1-(1-(but-2-ynoyl)pyrrolidin-3-yl)-3-(4-(2,6-difluorophenoxy)phenyl)-1 H-pyrrolo[2,3-d]pyridazin-7(6H)-one in any crystal form or amorphous form into an appropriate amount of organic solvent under heating, and then cooling the solution to precipitate a crystal; and 2) filtering the crystal, then washing and drying it. In step 1), the solvent is selected from any one or more of alcohols, ketones, nitriles, ethers, and esters, each of which has 4 or less carbon atoms, or a mixed solvent of one or more solvents mentioned above and water. The solvent is preferably methanol, ethanol, isopropanol, acetone, ethyl acetate, acetonitrile, tetrahydrofuran; or ethanol/water, N,N-dimethylformamide/water, or 1,4-dioxane/water. A single solvent or a mixed solvent of the organic solvents mentioned above can be used for crystallization.

Further, the single solvent is most preferably ethanol.

The recrystallization method is not particularly limited, and can be carried out by a conventional recrystallization process. For example, the material, i.e., the compound of formula (I), can be dissolved in an organic solvent under heating, then the solution is cooled slowly to precipitate a crystal under stirring. After the completion of crystallization, the desired crystal can be obtained via filtering and drying. In particular, the crystal obtained by filtration is usually dried in a vacuum under reduced pressure at a heating condition of about 30 to 100° C., preferably 40 to 60° C., to remove the recrystallization solvent.

The resulting crystal form is determined by differential scanning calorimetry (DSC) and X-ray diffraction spectrum. Meanwhile, the residual solvent in the obtained crystal is also determined.

The crystal of the compound of formula (I) prepared according to the method of the present invention does not contain or contains only a relatively low content of residual solvent, which meets the requirement of the National Pharmacopoeia concerning the limitation of the residual solvent of drug products. Therefore, the crystal of the present invention can be used well as an pharmaceutical active ingredient.

The experimental results show that under conditions of lighting, high temperature and high humidity, the stability of crystal form I of the compound of formula (I) prepared according to present invention is significantly better than the amorphous sample. Crystal form I is also stable under conditions of grinding, pressure and heating, which meets the medical needs of production, transportation and storage. The preparation process thereof is stable, repeatable and controllable, which is suitable for industrial production.

DETAILED DESCRIPTION OF THE INVENTION

Figure 1:
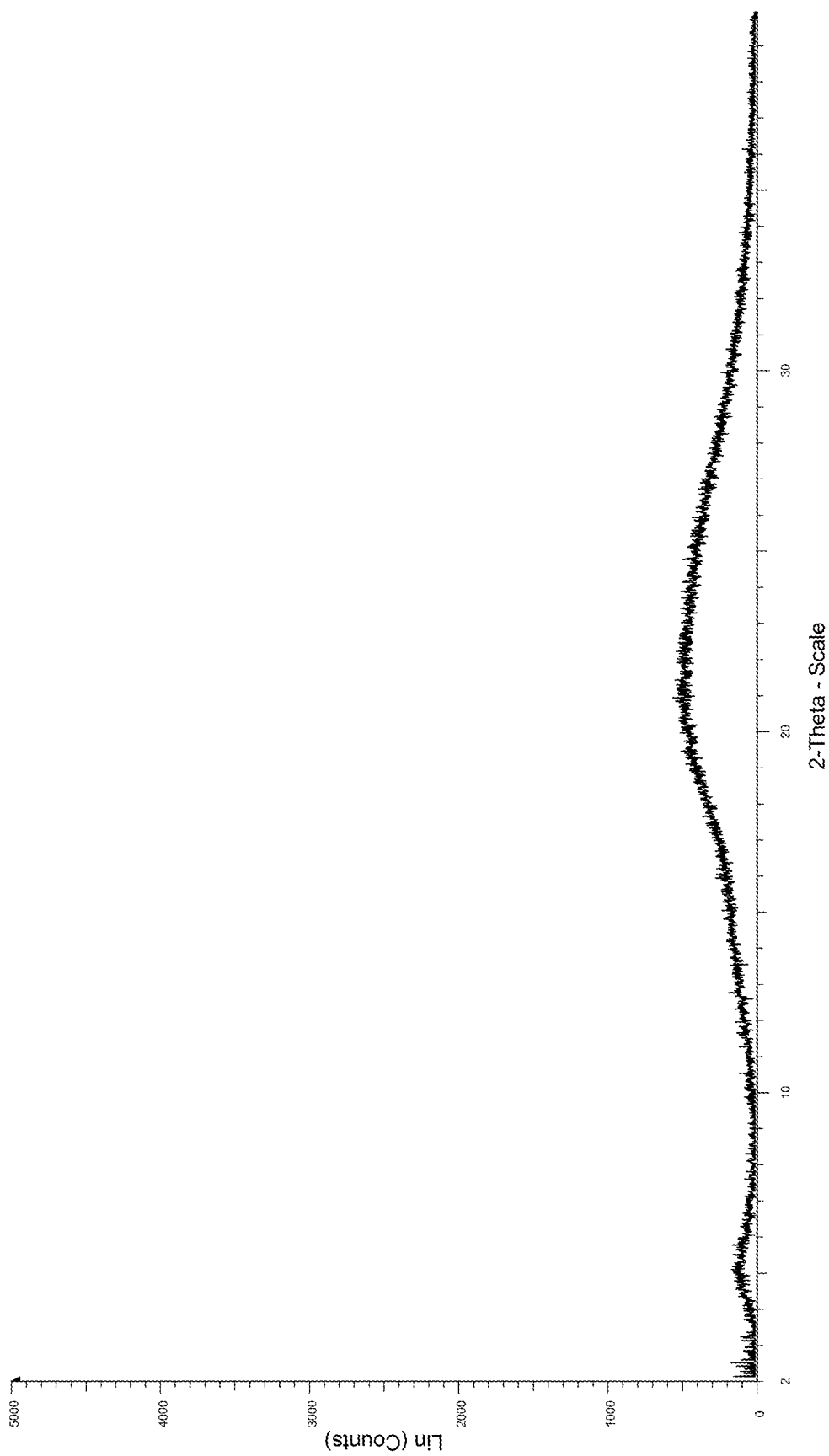
FIG. 1 shows the X-ray powder diffraction spectrum of an amorphous solid of the compound of formula (I).

The present invention is illustrated by the following examples in detail. The examples of the present invention are merely intended to describe the technical solution of the present invention, and should not be considered as limiting the scope of the present invention.

Testing instruments used in the experiments

1. DSC spectrum

Instrument type: Mettler Toledo DSC 1 Stare$^e$ System

Purging gas: Nitrogen

Heating rate: 10.0° C./min

Temperature range: 40-350° C.

2. X-ray diffraction spectrum

Instrument type: Bruker D8 Focus X-ray powder diffractometer

Ray: monochromatic Cu—Kα ray (λ=1.5406)

Scanning mode: θ/2θ, Scanning range: 2-40°

Voltage: 40 KV, Electric current: 40 mA

EXAMPLE 1

Preparation method of (R)-4-amino-1-(1-(but-2-ynoyl)pyrrolidin-3-yl)-3-(4-(2,6-difluorophenoxy)phenyl)-1H-pyrrolo[2,3-d]pyridazin-7(6H)-one, comprising the following three parts Part one: Preparation of compound 1b

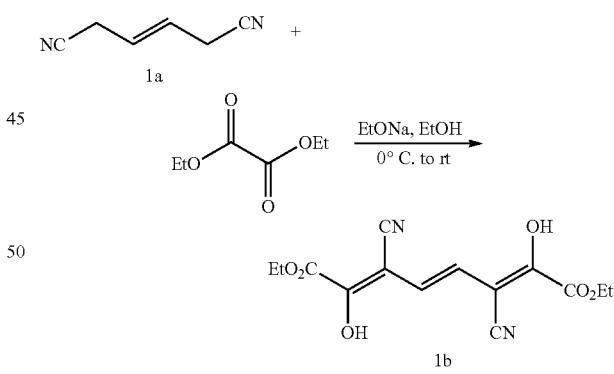

A solution of sodium acetate in ethanol (160 ml, the mass fraction is 21%, 0.49 mmol) was added to 110 ml of ethanol, and then diethyl oxalate (64 ml, 0.47 mol) was added in an ice bath. The mixture was stirred for 30 minutes. Then, a solution of (E)-hex-3-enenitrile 1a (16 g, 0.15 mmol) in ethanol (30 ml) was added, and the resulting mixture was stirred overnight at room temperature. After being cooled in an ice bath, the suspension was filtered. The solid was washed with a small amount of ethanol, and then dissolved in 380 ml of water. The solution was acidified by hydrochloric acid to pH 4, and then a large amount of solid was precipitated. The solid was filtered, washed with water, and dried to obtain 11.9 g of compound 1b as a yellow solid.

Part two: Preparation of compound 2

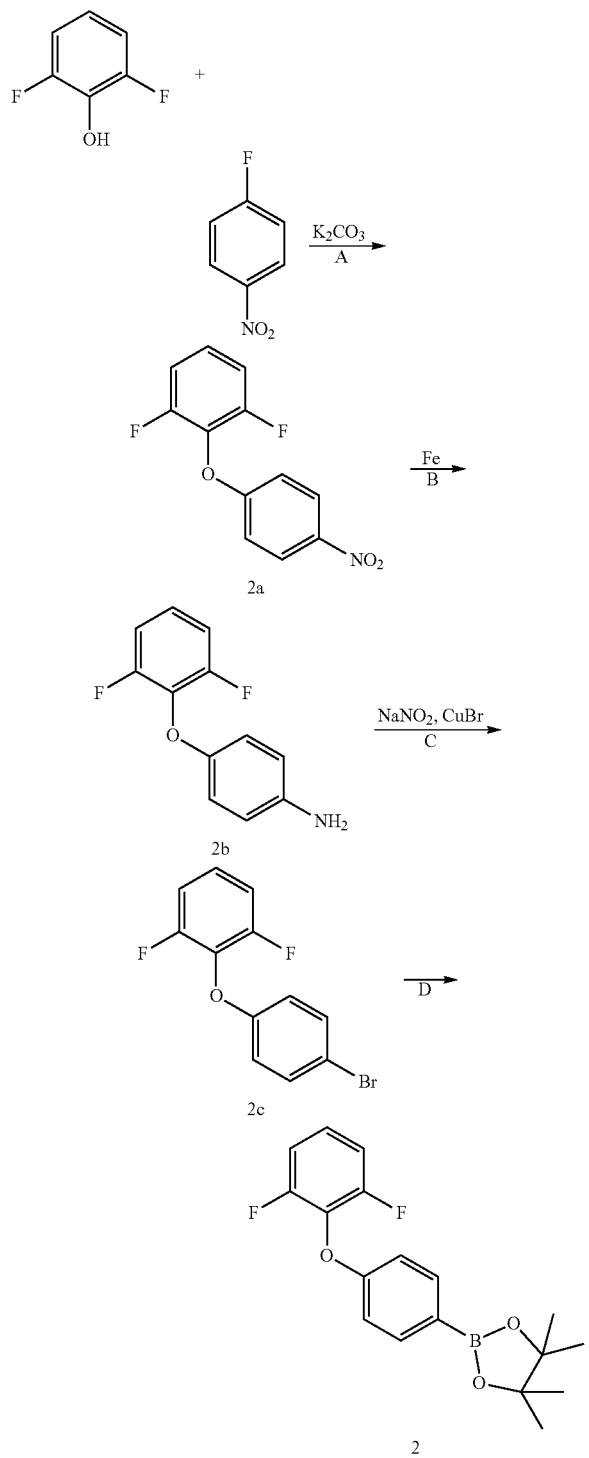

Step A 2,6-Difluorophenol (3.0 g, 21.3 mmol), 1-fluoro-4-nitrobenzene (3.04 g, 23.4 mmol) and potassium carbonate (4.4 g, 32 mmol) were added to 50 ml of acetonitrile, and the mixture was refluxed for 16 hours. After being cooled to room temperature, the solvents were removed. Water was added, and the mixture was extracted with ethyl acetate three times. The organic extracts were washed with water and brine, dried over magnesium sulfate, filtered, and concentrated to obtain 4.9 g of 1,3-Difluoro-2-(4-nitrophenoxy) benzene 2a as an oil.

Step B 1,3-Difluoro-2-(4-nitrophenoxy)benzene 2a (4.9 g, 19.5 mmol), 5 ml of saturated ammonium chloride solution and iron powder (5.5 g, 97.5 mmol) were added to 40 ml of methanol, and the mixture was refluxed for 3 hours. The mixture was filtered, then water was added to the filtrate, and the mixture was extracted with ethyl acetate three times. The organic extracts were washed with water and brine, dried over magnesium sulfate, filtered, and concentrated to obtain 4.1 g of 4-(2,6-Difluorophenoxy)aniline 2b as a light yellow oil.

MS (ESI): m/z=222.1 [M+H]$^+$.

Step C 4-(2,6-Difluorophenoxy)aniline 2b (4.1 g, 18.5 mmol) was added to 2M sulfuric acid solution (50 ml) at 0° C., then an aqueous solution (20 ml) of sodium nitrite (6.4 g, 92.7 mmol) was added. The mixture was stirred for 40 minutes, then copper bromide (5.3 g, 37 mmol) was added. The resulting mixture was refluxed for 16 hours. After being cooled to room temperature, the mixture was extracted with ethyl acetate three times. The organic extracts were washed with water and brine, dried over magnesium sulfate, filtered, and concentrated to obtain 1.6 g of 2-(4-Bromophenoxy)-1,3-difluorobenzene 2c as a colorless oil.

Step D 2-(4-Bromophenoxy)-1,3-difluorobenzene 2c (1.6 g, 3.6 mmol), bis(pinacolato)diboron (1.71 g, 6.7 mmol), KOAc (830 mg, 8.4 mmol) and Pd(PPh$_3$)$_2$Cl$_2$ (126 mg, 0.18 mmol) were added to 40 ml of 1,4-dioxane, and the mixture was stirred under nitrogen atmosphere at 80° C. for 16 hours. After being cooled to room temperature, the solvents were removed. The residue was purified by silica gel chromatography to obtain 1.6 g of 2 as a colorless oil.

Part 3: Preparation of (R)-4-amino-1-(1-(but-2-ynoyl)pyrrolidin-3-yl)-3-(4-(2,6-difluorophenoxy) phenyl)-1H-pyrrolo[2,3-d]pyridazin-7(6H)-one

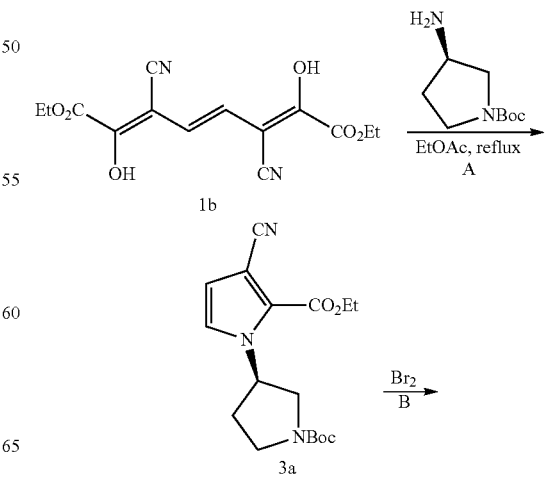

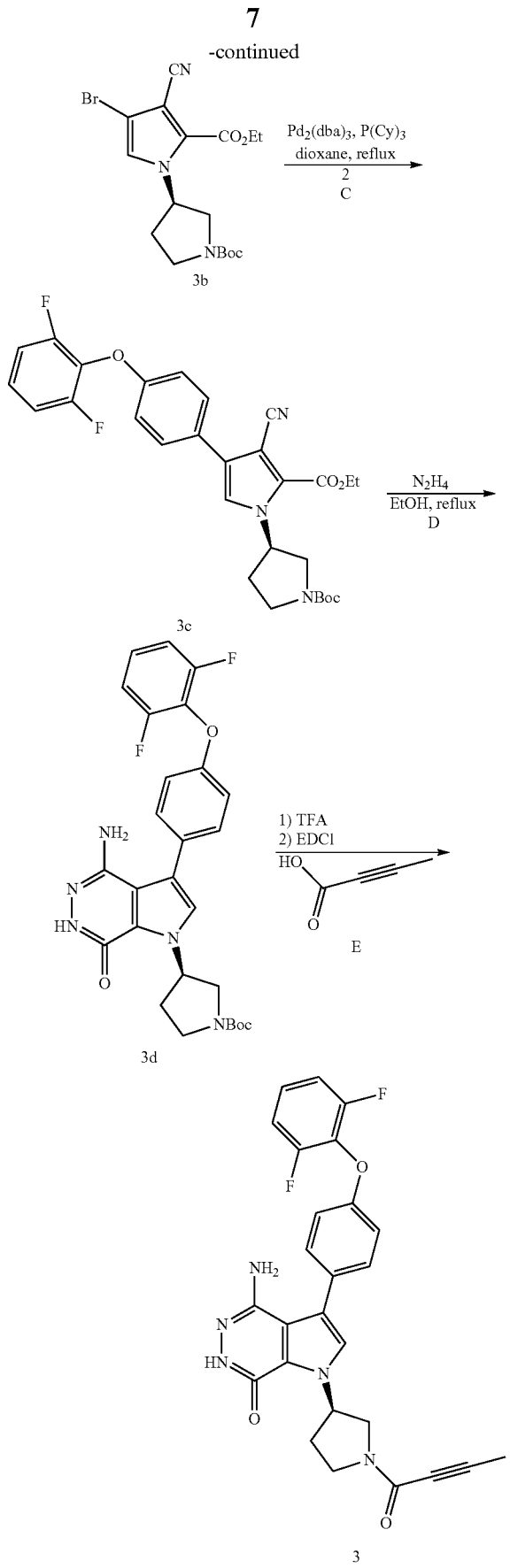

-continued

Step A 1.5 g of compound 1b was added to 84 ml of ethyl acetate, and the solution was heated to 60° C. Then a solution (21 ml) of (R)-1-tert-butoxycarbonyl-3-aminopyrrolidine (1.41 g) in ethyl acetate was added dropwise. The mixture was refluxed for 4 hours. After being cooled to room temperature, the solvents were removed. The residue was purified by silica gel chromatography to obtain 0.686 g of compound 3a.

Step B 0.686 g of compound 3a was added to 120 ml of dichloromethane at 0° C., and a solution (5 ml) of $Br_2$ (3.7 g) in dichloromethane was slowly added dropwise. The mixture was stirred for 1.5 hours, and then quenched with 10% sodium thiosulfate solution and saturated sodium bicarbonate solution. The two phases were separated, and the aqueous phase was extracted with dichloromethane. The combined organic extracts were treated with excess $Boc_2O$, dried over sodium sulfate, filtered and concentrated. The residue was purified by silica gel chromatography to obtain 0.342 g of compound 3b.

Step C

Compound 3b (198 mg, 0.48 mmol), compound 2 (160 mg, 0.48 mmol) and $K_3PO_4.3H_2O$ (188 mg, 0.72 mmol) were added to 1,4-dioxane/water (10 ml/1 ml) under nitrogen atmosphere. Then, $Pd_2(dba)_3$ (22 mg, 0.024 mmol) and $P(Cy)_3$ (14 mg, 0.048 mmol) were added. The resulting mixture was refluxed under nitrogen atmosphere for 16 hours. After cooling to room temperature, the mixture was filtered and the filtrate was concentrated. The residue was purified by silica gel chromatography to obtain 59 mg of 3c as a white solid.

MS (ESI): m/z=538 [M+H]$^+$.

Step D

Compound 3c (72 mg, 0.13 mmol) and 1 ml of $N_2H_4.H_2O$ were added to 5 ml of ethanol, and the mixture was refluxed for 16 hours. After being cooled to room temperature, the solvents were removed. The residue was purified by silica gel chromatography to obtain 24 mg of compound 3d as a white solid.

MS (ESI): m/z=524 [M+H]$^+$.

Step E

Figure 2:
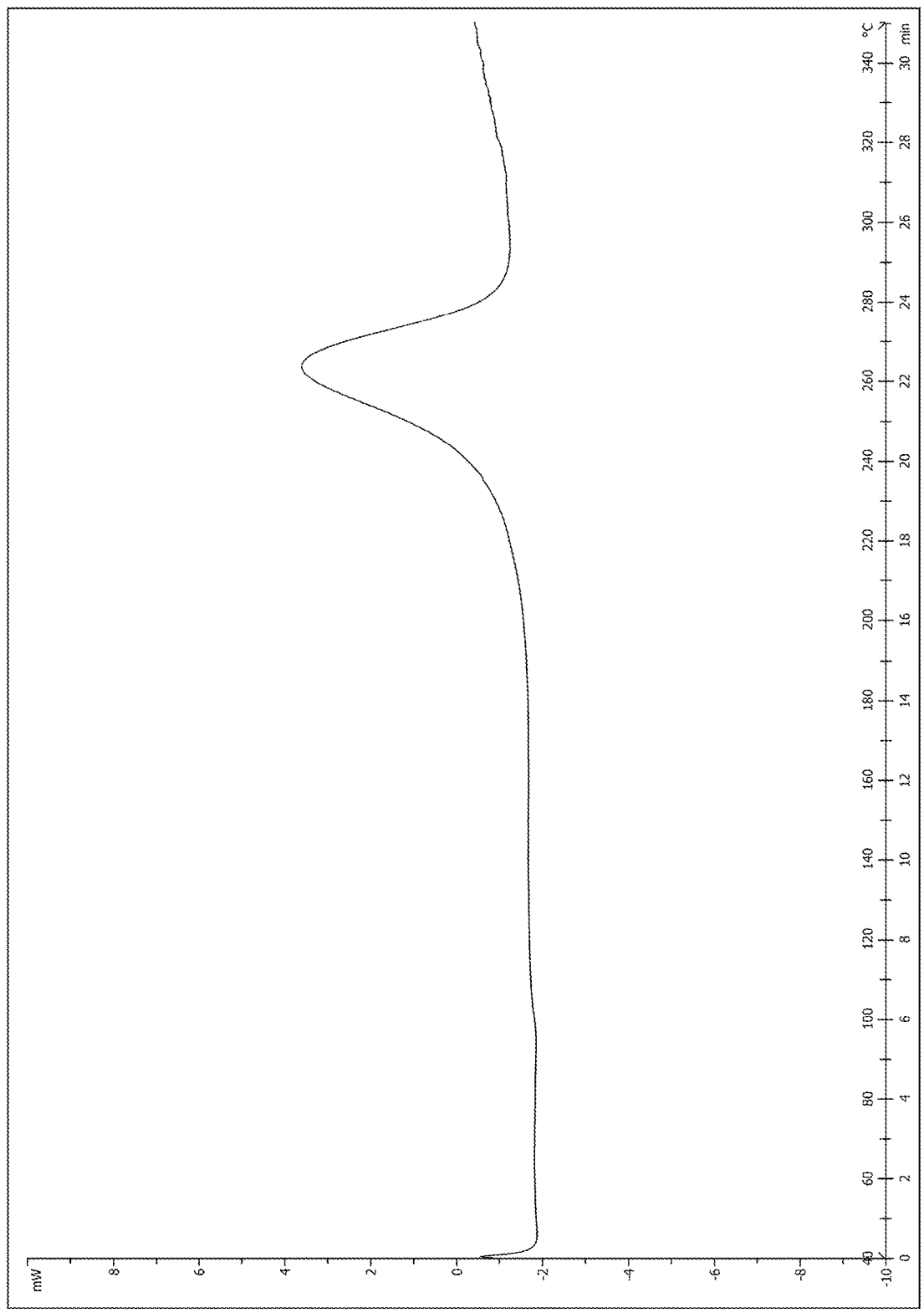
FIG. 2 shows the DSC spectrum of an amorphous solid of the compound of formula (I).

Compound 3d (40 mg, 0.08 mmol) was added to 5 ml of dichloromethane, and then 1 ml of trifluoroacetic acid was added. The mixture was stirred at room temperature for 3 hours, and then concentrated to obtain 49 mg of compound 3e as an oil. But-2-ynoic acid (13 mg, 0.16 mmol), carbodiimide (31 mg, 0.16 mmol) and trifluoroacetic anhydride (17 mg, 0.16 mmol) were added to a solution (5 ml) of compound 3e (49 mg) in dichloromethane. The resulting mixture was stirred at room temperature for 18 hours and concentrated. The residue was purified by silica gel chromatography to obtain 20 mg of the title compound 3 as a white solid. The X-ray diffraction spectrum of the solid sample is shown in FIG. 1, in which there are no characteristic absorption peaks of a crystal. The DSC spectrum of the solid sample is shown in FIG. 2, in which there is no melting endothermic peak below 350° C. The product was thus identified as an amorphous solid.

MS (ESI): m/z=490 [M+H]$^+$.

EXAMPLE 2

Figure 3:
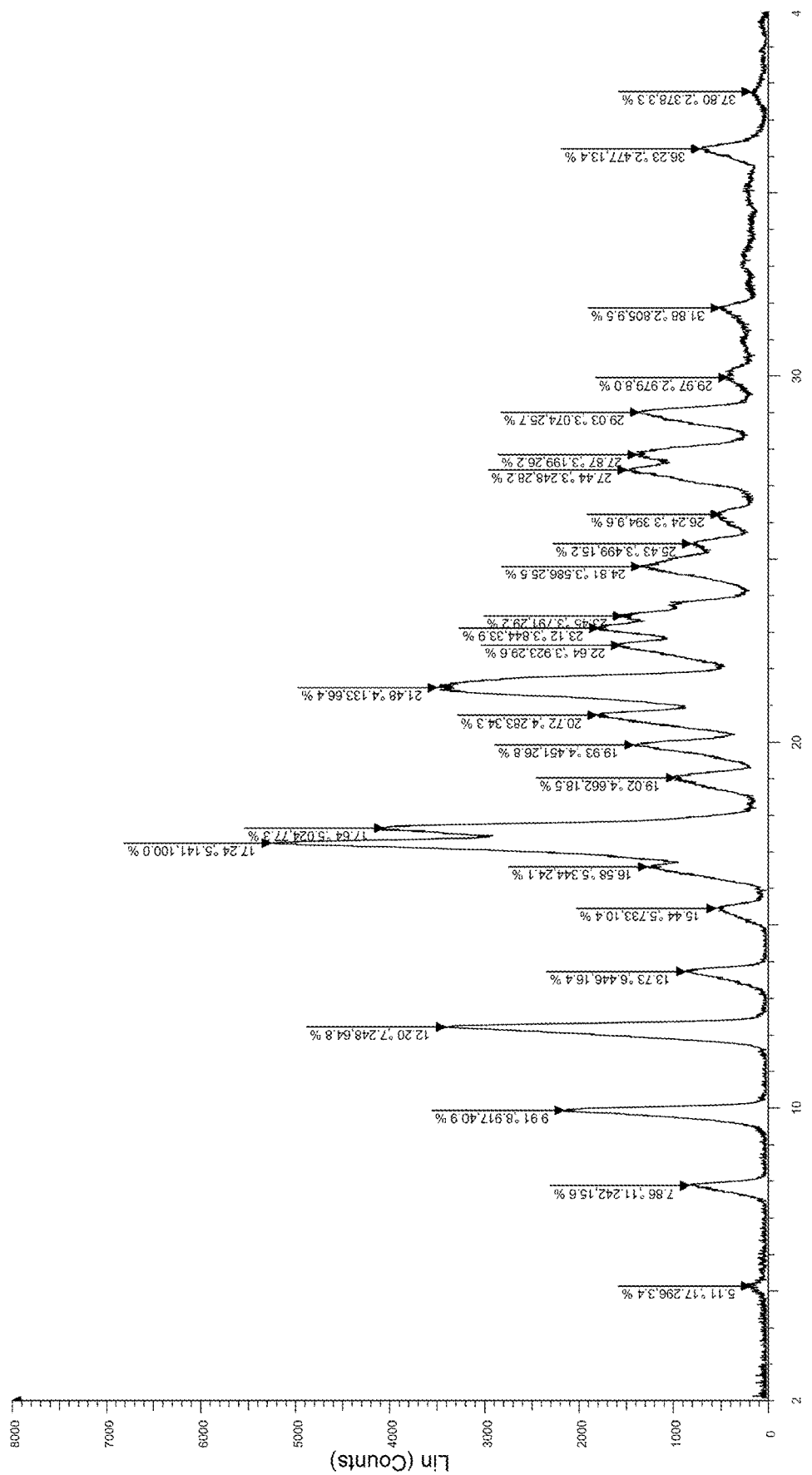
FIG. 3 shows the X-ray powder diffraction spectrum of crystal form I of the compound of formula (I).
Figure 4:
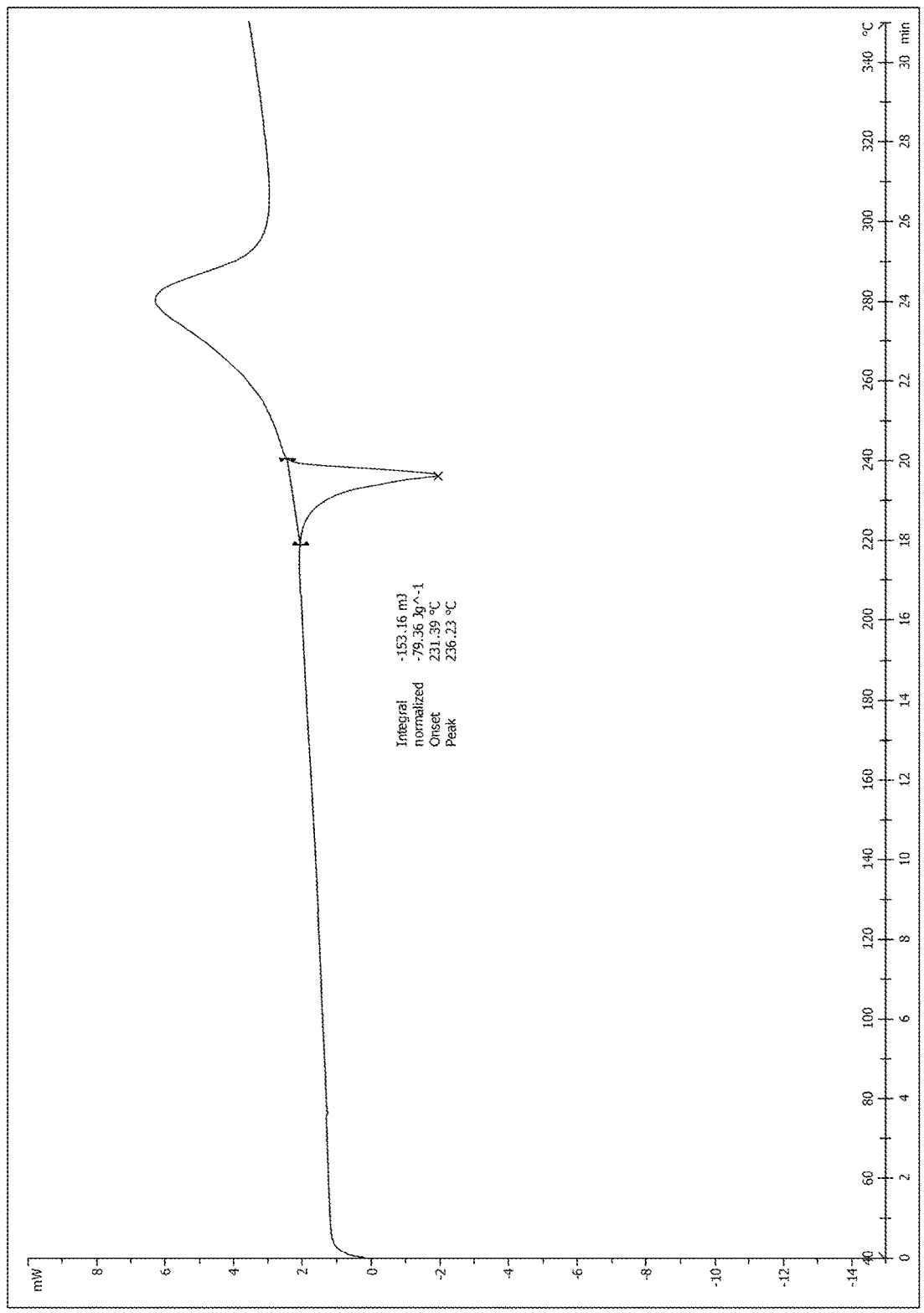
FIG. 4 shows the DSC spectrum of crystal form I of the compound of formula (I).

The compound of formula (I) (1.0 g, 2.04 mmol) (prepared according to Example 1) was added to a 50 ml one-necked flask, followed by addition of 15 ml of anhydrous ethanol. The mixture was heated to reflux until the solution was clear. The solution was cooled, and then a large amount of solid was precipitated. The mixture was filtered and dried to obtain a solid (805 mg, yield: 80.5%). The X-ray powder diffraction spectrum of the crystal sample is shown in FIG. 3, in which there are characteristic peaks at 2θ±0.2: about 5.11 (17.30), 7.86 (11.24), 9.91 (8.92), 12.20 (7.25), 13.73 (6.45), 15.44 (5.73), 17.24 (5.14), 17.64 (5.02), 19.02 (4.66), 19.93 (4.45), 20.72 (4.28), 21.48 (4.13), 22.64 (3.92), 23.12 (3.84), 24.81 (3.59), 25.43 (3.50), 26.24 (3.39), 27.44 (3.25), 27.87 (3.20), and 29.03 (3.07). The DSC spectrum is shown in FIG. 4, having a sharp melting endothermic peak at 236.23° C. The crystal form was defined as crystal form I.

EXAMPLE 3

The compound of formula (I) (1.0 g, 2.04 mmol) (prepared according to Example 1) was added to a 50 ml one-necked flask, followed by addition of 15 ml of anhydrous methanol. The mixture was heated to reflux until the solution was clear. The solution was cooled, and then a large amount of solid was precipitated. The mixture was filtered and dried to obtain a solid (765 mg, yield: 76.5%). The product was identified as crystal form I after studying and comparing the X-ray diffraction and DSC spectra.

EXAMPLE 4

The compound of formula (I) (1.0 g, 2.04 mmol) (prepared according to Example 1) was added to a 50 ml one-necked flask, followed by addition of 15 ml of isopropanol. The mixture was heated to reflux until the solution was clear. The solution was cooled, and then a large amount of solid was precipitated. The mixture was filtered and dried to obtain a solid (745 mg, yield: 74.5%). The product was identified as crystal form I after studying and comparing the X-ray diffraction and DSC spectra.

EXAMPLE 5

The compound of formula (I) (1.0 g, 2.04 mmol) (prepared according to Example 1) was added to a 50 ml one-necked flask, followed by addition of 10 ml of ethyl acetate. The mixture was heated to reflux until the solution was clear. The solution was cooled, and then a large amount of solid was precipitated. The mixture was filtered and dried to obtain a solid (690 mg, yield: 69.0%). The product was identified as crystal form I after studying and comparing the X-ray diffraction and DSC spectra.

EXAMPLE 6

The compound of formula (I) (1.0 g, 2.04 mmol) (prepared according to Example 1) was added to a 50 ml one-necked flask, followed by addition of 10 ml of acetone. The mixture was heated to reflux until the solution was clear. The solution was cooled, and a large amount of solid was precipitated. The mixture was filtered and dried to obtain a solid (660 mg, yield: 66.0%). The product was identified as crystal form I after studying and comparing the X-ray diffraction and DSC spectra.

EXAMPLE 7

The compound of formula (I) (1.0 g, 2.04 mmol) (prepared according to Example 1) was added to a 50 ml one-necked flask, followed by addition of 10 ml of acetonitrile. The mixture was heated to reflux until the solution was clear. The solution was cooled, and then a large amount of solid was precipitated. The mixture was filtered and dried to obtain a solid (810 mg, yield: 81.0%). The product was identified as crystal form I after studying and comparing the X-ray diffraction and DSC spectra.

EXAMPLE 8

The compound of formula (I) (1.0 g, 2.04 mmol) (prepared according to Example 1) was added to a 25 ml one-necked flask, followed by addition of 3 ml of tetrahydrofuran. The mixture was heated to reflux until the solution was clear. The solution was cooled, and then a large amount of solid was precipitated. The mixture was filtered and dried to obtain a solid (587 mg, yield: 58.7%). The product was identified as crystal form I after studying and comparing the X-ray diffraction and DSC spectra.

EXAMPLE 9

The compound of formula (I) (1.0 g, 2.04 mmol) (prepared according to Example 1) was added to a 25 ml one-necked flask, followed by addition of 7 ml of ethanol/water (V:V=1:1). The mixture was heated to reflux until the solution was clear. The solution was cooled, and then a large amount of solid was precipitated. The mixture was filtered and dried to obtain a solid (657 mg, yield: 65.7%). The product was identified as crystal form I after studying and comparing the X-ray diffraction and DSC spectra.

EXAMPLE 10

The compound of formula (I) (1.0 g, 2.04 mmol) (prepared according to Example 1) was added to a 25 ml one-necked flask, followed by addition of 7 ml of N,N-dimethylformamide/water (V:V=1:1). The mixture was heated to reflux until the solution was clear. The solution was cooled, and then a large amount of solid was precipitated. The mixture was filtered and dried to obtain a solid (600 mg, yield: 60.0%). The product was identified as crystal form I after studying and comparing the X-ray diffraction and DSC spectra.

EXAMPLE 11

The compound of formula (I) (1.0 g, 2.04 mmol) (prepared according to Example 1) was added to a 25 ml one-necked flask, followed by addition of 10 ml of 1,4-dioxane/water (V:V=1:2). The mixture was heated to reflux until the solution was clear. The solution was cooled, and then a large amount of solid was precipitated. The mixture was filtered and dried to obtain a solid (793 mg, yield: 79.3%). The product was identified as crystal form I after studying and comparing the X-ray diffraction and DSC spectra.

EXAMPLE 12

The sample of amorphous form prepared in Example 1 and the sample of crystal form I prepared in Example 2 were spread flat in the air to test their stability under conditions of lighting (4500 Lux), heating (40° C., 60° C.), and high humidity (RH 75%, RH 90%), respectively. Samplings were carried out on Day 5 and Day 10. The purity as detected by HPLC is shown in Table 1.

TABLE 1

Stability comparison of crystal form I and an amorphous sample of the compound of formula (I)

| Batch number | Time (day) | Lighting | 40° C. | 60° C. | RH 75% | RH 90% |
|---|---|---|---|---|---|---|
| Crystal form I 20150323 | 0 | 99.21% | 99.21% | 99.21% | 99.21% | 99.21% |
| | 5 | 99.26% | 99.28% | 99.26% | 99.30% | 99.30% |
| | 10 | 99.25% | 99.35% | 99.25% | 99.25% | 99.32% |
| Amorphous form 20150331 | 0 | 97.70% | 97.70% | 97.70% | 97.70% | 97.70% |
| | 5 | 97.67% | 97.64% | 97.68% | 97.52% | 97.50% |
| | 10 | 97.62% | 97.57% | 97.52% | 97.59% | 97.48% |

After crystal form I and the amorphous sample were spread flat in the air to test and compare their stability under the conditions of lighting, high temperature, and high humidity, the results of the stability study showed that the stability of crystal form I was significantly better than that of the amorphous sample under conditions of lighting, high temperature and high humidity.

EXAMPLE 13

Crystal form I of the compound of formula (I) prepared according to the method of Example 2 was ground, heated and tableted. The results showed that the crystal form was stable. The detailed experimental data are shown in Table 2 below.

TABLE 2

Special stability study of crystal form I of the compound of formula (I)

| Batch number | Treatment Process | Experimental procedure | Crystal form | DSC peak |
|---|---|---|---|---|
| 20150427G | Grinding treatment for 10 minutes | 1 g of the sample of crystal form I of the compound of formula (I) was ground for 10 minutes in a mortar under nitrogen atmosphere. | Crystal form I | 239.32° C. |
| 20150427H | Heating treatment for 3 hours at 80° C. | 1 g of the sample of crystal form I of the compound of formula (I) was spread flat and heated at 80° C. for 3 hours. | Crystal form I | 238.98° C. |
| 20150427P | Tableting treatment | The sample of crystal form I of the compound of formula (I) was tableted. | Crystal form I | 241.19° C. |

What is claimed is:

1. Crystal form I of (R)-4-amino-1-(1-(but-2-ynoyl)pyrrolidin-3-yl)-3-(4-(2,6-difluorophenoxy)phenyl)-1H-pyrrolo[2,3-d]pyridazin-7(6H)-one, characterized by a characteristic X-ray powder diffraction spectrum comprising peaks at diffraction angles 2θ±0.2 of 9.91, 12.20, 17.24, 17.64, and 21.48.

2. The crystal form I according to claim 1, wherein the X-ray powder diffraction spectrum comprises peaks at diffraction angles 2θ±0.2 of 7.86, 9.91, 12.20, 13.73, 17.24, 17.64, 19.02, 19.93, 20.72, 21.48, 22.64, 24.81, 27.44, and 27.87.

3. The crystal form I according to claim 1, wherein the X-ray powder diffraction spectrum comprises peaks at diffraction angles 2θ±0.2 of about 5.11, 7.86, 9.91, 12.20, 13.73, 15.44, 17.24, 17.64, 19.02, 19.93, 20.72, 21.48, 22.64, 23.12, 24.81, 25.43, 26.24, 27.44, 27.87, and 29.03.

4. A method of preparing the crystal form I of (R)-4-amino-1-(1-(but-2-ynoyl)pyrrolidin-3-yl)-3-(4-(2,6-difluorophenoxy)phenyl)-1H-pyrrolo[2,3-d]pyridazin-7(6H)-one according to claim 1, comprising:

1) dissolving a solid (R)-4-amino-1-(1-(but-2-ynoyl)pyrrolidin-3-yl)-3-(4-(2,6-difluorophenoxy)phenyl)-1H-pyrrolo[2,3-d]pyridazin-7(6H)-one in any crystal form or amorphous form in an organic solvent under heating to obtain a solution, and then cooling the solution to precipitate a crystal, wherein the solvent is selected from any one or more of alcohols, ketones, nitriles, ethers, and esters, each of which has 4 or less carbon atoms, or a mixed solvent of water and one or more solvents selected from any one or more of alcohols, ketones, nitriles, ethers, and esters, each of which has 4 or less carbon atoms; and 2) filtering the crystal, then washing, and drying the crystal.

5. The method according to claim 4, wherein the solvent is methanol, ethanol, isopropanol, acetone, ethyl acetate, acetonitrile, tetrahydrofuran, a mixed solvent of ethanol and water, a mixed solvent of N,N-dimethylformamide and water, or a mixed solvent of 1,4-dioxane and water.

6. The method according to claim 5, wherein the solvent is ethanol.

7. A pharmaceutical composition comprising the crystal form I of (R)-4-amino-1-(1-(but-2-ynoyl)pyrrolidin-3-yl)-3-(4-(2,6-difluorophenoxy)phenyl)-1H-pyrrolo[2,3-d]pyridazin-7(6H)-one according to claim 1, and a pharmaceutically acceptable carrier.

8. A crystal form I of (R)-4-amino-1-(1-(but-2-ynoyl)pyrrolidin-3-yl)-3-(4-(2,6-difluorophenoxy)phenyl)-1H-pyrrolo[2,3-d]pyridazin-7(6H)-one, wherein the crystal form I has a characteristic X-ray powder diffraction spectrum as shown in FIG. 3.

9. A method of treating B-cell malignancies and autoimmune diseases, comprising administering to a subject the pharmaceutical composition according to claim 7.

10. A pharmaceutical composition comprising the crystal form I of (R)-4-amino-1-(1-(but-2-ynoyl)pyrrolidin-3-yl)-3-(4-(2,6-difluorophenoxy)phenyl)-1H-pyrrolo[2,3-d]pyridazin-7(6H)-one according to claim 8, and a pharmaceutically acceptable carrier.

11. A method of treating B-cell malignancies and autoimmune diseases, comprising administering to a subject the pharmaceutical composition according to claim 10.

* * * * *